United States Patent [19]

Morita et al.

[11] Patent Number: 5,256,655
[45] Date of Patent: Oct. 26, 1993

[54] BICYCLIC SULFUR-CONTAINING COMPOUNDS

[75] Inventors: Takakazu Morita, Toyonaka; Shiro Mita, Ashiya; Yoichi Kawashima, Kyoto, all of Japan

[73] Assignee: Santen Pharmaceutical Co., Ltd., Osaka, Japan

[21] Appl. No.: 969,405

[22] Filed: Oct. 30, 1992

Related U.S. Application Data

[62] Division of Ser. No. 718,220, Jun. 20, 1991, Pat. No. 5,183,816.

[30] Foreign Application Priority Data

Jul. 3, 1990 [JP] Japan .................. 2-175782

[51] Int. Cl.$^5$ .................. A61K 31/55; C07D 281/18; C07D 513/04
[52] U.S. Cl. .................. 514/211; 514/183; 540/468; 540/552
[58] Field of Search .............. 540/468, 552; 514/183, 514/211

[56] References Cited

FOREIGN PATENT DOCUMENTS 1412996  11/1975  United Kingdom ............. 544/48

OTHER PUBLICATIONS

J. Borgulya et al., "Rearrangment of Derivatives of 1,3-Dithian-5-amine into Bicyclic 2-Thiazolidines.", Helv. Chem. Acta, 67, pp. 1827–1842 (1984).

*Primary Examiner*—Mukund J. Shah
*Assistant Examiner*—Y. N. Gupta
*Attorney, Agent, or Firm*—Frishauf, Holtz, Goodman & Woodward

[57] ABSTRACT

Compounds of the formula [I] and salts thereof, which are useful for treatment of liver disorders,

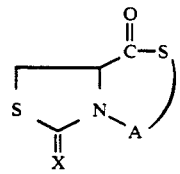

wherein
X is oxygen or sulfur; and
A is straight $C_3$–$C_4$ alkylene which can be substituted by one or more lower alkyl groups.

12 Claims, No Drawings

BICYCLIC SULFUR-CONTAINING COMPOUNDS

This is a division of application Ser. No. 07/718,220 filed Jun. 20, 1991, now U.S. Pat. No. 5,183,816 issued Feb. 2, 1993.

DETAILED DESCRIPTION OF THE INVENTION

This invention relates to the compounds of the formula [I] and salts thereof (hereinafter referred to as the "Compound"), which are useful for treatment of liver disorders.

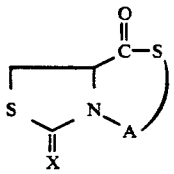

wherein

X is oxygen or sulfur; and

A is straight $C_2$-$C_4$ alkylene which can be substituted by one or more lower alkyl.

The same shall be applied hereinafter.

The term "lower alkyl" intends to designate straight or branched $C_1$-$C_6$ alkyl exemplified by methyl, ethyl, propyl, isopropyl and hexyl.

The Compound can be converted into pharmaceutically acceptable salts. Examples of the salts are hydrochloric acid salt, sulfuric acid salt, phosphoric acid salt and maleic acid salt.

There are few studies on bicyclic compounds in which thiazolidine-2-thione or -2-one is condensed with a heterocycle having a sulfur atom. Only Borgulya J. et al. reported such bicyclic compounds (Helv. Chim. Acta, 67, p. 1827 (1984)). They studied the conversion reaction from 1,3-dithian-5-amine derivatives to bicylic-2-thiazolidine derivatives and synthesized 7,7a-dihydro-1H,3H,5H-thiazoro[3,4-c]-thiazole-3-one derivatives.

Synthetic studies of such bicyclic compounds are very important to find novel compounds having an unique ring system. Thereupon, we studied synthetic methods of bicyclic sulfur-containing compounds and have succeeded in obtaining various novel compounds. Furthermore, we studied applications of the Compound to drugs and found that the Compound, which has novel chemical structures condensed by thiazolidine-2-thione or -2-one with heterocycle having a sulfur atom, a nitrogen atom and a carbonyl group, would be useful for treatment of liver disorders.

The Compound can be prepared by such methods as the follows.

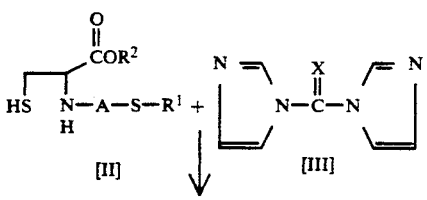

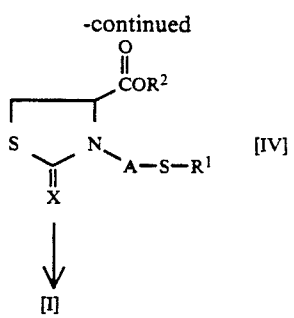

Wherein, $R^1$ is a protective group of thiol such as p-methoxybenzyl; and $R^2$ is hydrogen or lower alkyl.

The compound of the formula [I] can be prepared by a cyclization reaction of the compound of the formula [IV] using strong acid such as trifluoromethanesulfonic acid in trifluoroacetic acid etc. The compound of the formula [IV] can be prepared by a reaction of the compound of the formula [II] with the compound of the formula [III].

No specific conditions are necessary for the above reaction but the known methods generally used for such reaction are applicable.

The Compound has stereoisomers because of the existence of one or more asymmetric carbon atom, and these isomers are included in this invention.

The Compound, a novel bicyclic compound, is useful as a medical substance, especially for treatment of liver disorders such as acute hepatic failure, acute hepatitis, chronic hepatitis and liver cirrhosis.

The acute hepatic failure model reported by Feruluga J. et al., (Agent and Actions, 9, 566 (1979)) is well known as an animal model to examine effects of a drug on liver disorders. We examined effects of the Compound on liver disorders using this model. As the result of our experiment, we found that the mortality of the animal group treated with the Compound was lower than that of the control group. The result proves that the Compound is useful for treatment of liver disorders.

The Compound can be administered either orally or parenterally. Examples of dosage forms are tablet, capsule, powders, granules, injection and the percutaneous. The dosage is adjusted depending on symptom, dosage form, etc., but usual daily dosage is 1 to 5000 mg in one or a few divided doses.

Examples of formulations are shown below.

1) Tablet

The following tablet can be prepared by a usual method.

| | |
|---|---|
| Compound | 100 mg |
| crystalline cellulose | 20 mg |
| lactose | 40 mg |
| hydroxypropylcellulose | 5 mg |
| magnesium stearate | 5 mg |
| total | 170 mg |

2) capsule

The following capsule can be prepared by a usual method.

| | |
|---|---|
| Compound | 5 mg |
| lactose | 142 mg |

| | |
|---|---|
| -continued | |
| magnesium stearate | 3 mg |
| total | 150 mg |

By changing the ratio of the Compound and lactose, capsules which contains 10 mg, 30 mg, 50 mg or 100 mg of the Compound, can be prepared.

3) granules

The following granules can be prepared by a usual method.

| | |
|---|---|
| Compound | 50 mg |
| lactose | 55 mg |
| starch | 20 mg |
| hydroxypropylcellulose | 4 mg |
| talc | 1 mg |
| total | 130 mg |

Examples of preparations of the Compound are shown below.

EXAMPLE

Example 1

(6S)-1-Aza-3,3-dimethyl-4,8-dithiabicyclo[4,3,0]nonan-5-on-9-thione

To a solution of N-[2-(4-methoxybenzylthio)-2-methylpropyl]L-cysteine methyl ester (5.0 g) in chloroform (90ml), thiocarbonyldiimidazole (3.0 g) was added and the mixture was stirred for 1.5 hr at room temperature. The reaction mixture was washed with 3N hydrochloric acid, water and then saturated sodium chloride solution, dried over anhydrous magnesium sulfate, and concentrated in vacuo. The oily residue was purified by a silica gel column chromatography to give 5.10 g(91%) of (4R)-3-[2-( 4-methoxy-benzylthio)-2-methylpropyl]-4-methoxycarbonylthiazolidine-2-thione To a solution of the above product (2.5 g) in trifluoroacetic acid (10 ml), thioanisole (1.52 ml) and trifluoromethanesulfonic acid (2.29 ml) were added and the mixture was stirred for 30 minutes at room temperature. The reaction mixture was neutralized with sodium bicarbonate and extracted with ethyl acetate. The organic layer was washed with water and saturated sodium chloride solution, dried over anhydrous magnesium sulfate, and concentrated in vacuo. The oily residue was purified by a silica gel column chromatography. The crude product was recrystallized from n-hexane—ethyl acetate to give 0.42 g (27.8%) of the titled compound.

m.p. 126°-128°0 C. (n-hexane—ethyl acetate)
$[\alpha]_D^{25}$ −24.6° (c=1.0, chloroform)
IR (KBr, cm$^{-1}$) 2936, 1664, 1423, 1350, 1280, 1206, 1169, 1130, 1056, 1011, 690

By the similar method as Example 1, following compounds were obtained.

(6S)-1-Aza-3-methyl-4,8-dithiabicyclo[4,3,0]nonan-5-on-9-thione m.p 124°-125° C. (n-hexane—ethyl acetate)
IR (KBr, cm$^{-1}$) 2980, 2932, 2844, 1675, 1419, 1282, 1211, 1203, 1154, 1058, 982, 958, 705

(7S)-1-Aza-3,3-dimethyl-5,9-dithiabicyclo[5,3,0]decan-6-on-10-thione m.p. 184°-186° C. (chloroform)
$[\alpha]_D^{25}$ +93.5° (c=1.0, chloroform)
IR (KBr, cm$^{-1}$) 1659, 1449, 1402, 1264, 1199, 1166, 1050, 1039

(6S)-1-Aza-4,8-dithiabicyclo[4,3,0]nonan-5-on-9-thione m.p. 146°-159° C. (n-hexane—ethyl acetate)
$[\alpha]_D^{25}$ +26.8° (c=0.35, chloroform)
IR (KBr, cm$^{-1}$) 2990, 2855, 1675, 1437, 1420, 1350, 1310, 1263, 1225, 1054, 1006, 972, 879, 716

(6S)-1-Aza-3,3-diethyl-4,8-dithiabicyclo[4,3,0]nonan-5-on-9-thione m.p. 106°-107° C. (diisopropylether)
$[\alpha]_D^{25}$ −1.8° (c=0.2, chloroform)
IR (KBr, cm$^{-1}$) 2959, 1676, 1460, 1418, 1273, 1228, 1167, 1060, 1030, 1002, 887, 686

Example 2

(6S)-1-Aza-3,3-dimethyl-4,8-dithiabicyclo[4,3,0]nonan-5,9-dione

To a solution of N-[2-(4-methoxybenzylthio)-2-methylpropyl]L-cysteine methyl ester (0.6 g) in dimethylformamide (DMF,10 ml), carbonyldiimidazole (0.34 g) was added and the mixture was stirred for 2.5 hr at 110°-120° C. After the addition of hydrochloric acid to the reaction mixture, the mixture was extracted with ethyl acetate. The organic layer was washed with 1N hydrochloric acid, water and then saturated sodium chloride solution, dried over anhydrous magnesium sulfate, and concentrated in vacuo. The oily residue was purified by a silica gel column chromatography to give 0.35 g of (4R)-3-[2-(4-methoxybenzylthio)-2-methylpropyl]-4-methoxycarbonylthiazolidine-2-one.

To a solution of the above product (0.33 g) in trifluoroacetic acid (2 ml), thioanisole (0.21 ml) was added, and then trifluoromethanesulfonic acid (0.16 ml) was added dropwise under ice-cooling and the mixture was stirred for 15 minutes under ice-cooling. The reaction mixture was neutralized with sodium bicarbonate and extracted with ethyl acetate. The organic layer was washed with saturated sodium bicarbonate solution, water and then saturated sodium chloride solution, dried over anhydrous magnesium sulfate, and concentrated in vacuo. The oily residue was purified by a silica gel column chromatography. The crude product was recrystallized from n-hexane—ethyl acetate to give 0.14 g (63.6%) of the titled compound.

m.p. 137°-138° C. (n-hexane—ethyl acetate)
$[\alpha]_D^{25}$ −124.1° (c=1.0, chloroform)
IR (KBr, cm$^{-1}$) 2972, 1685, 1386, 1355, 1306, 1275, 1212, 1123, 1082, 819

PHARMACOLOGICAL TEST

The acute hepatic failure model reported by Feruluga J. et al., (Agent and Actions, 9, 566 (1979)) is well known as an animal model to examine effects of a drug on liver disorders. We examined effects of the Compound on liver disorders using this model.

Experimental Method

According to the method described in the literature, 0.7 mg/mouse of Propionibacterium acnes was injected intravenously into male BALB/c strain mice (8 weeks old). Seven days later, the Compound suspended in 1% methylcellulose solution was administered orally at a dose of 100 mg/kg. To a control group, 1% methylcellulose solution alone was administered. One hour later, 25μg of lipopolysaccharide was injected intravenously, and then the mortality was recorded during 48 hours.

Result

The mortality of the group treated with the Compound was lower than that of the control group.

What we claim is:

1. A compound of the formula [I] and salts thereof,

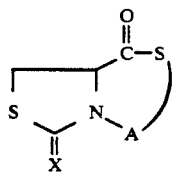

wherein

X is oxygen or sulfur; and

A is straight $C_{14}$-$C_4$ alkylene which can be substituted by one or more lower alkyl groups.

2. (7S)-1-Aza-3,3-dimethyl-5,9-dithiabicyclo[5,3,0]decan-6-one-10-thione.

3. The compound as in claim 1, wherein A is $C_3$ alkylene.

4. The compound as in claim 1, wherein A is $C_4$ alkylene.

5. The compound as in claim 1, wherein A is a straight $C_3$-$C_4$ alkylene which is substituted by one or more $C_1$-$C_6$ alkyl groups.

6. The compound as in claim 5, wherein A is $C_3$-$C_4$ alkylene substituted by a methyl group.

7. The compound as in claim 5, wherein A is $C_3$-$C_4$ alkylene substituted by an ethyl group.

8. The compound as in claim 1, wherein X is oxygen.

9. The compound as in claim 1, wherein X is sulfur.

10. A pharmaceutical composition comprising a compound of the formula [I] as in claim 1 or pharmaceutically acceptable salts thereof and a pharmaceutically acceptable carrier therefore.

11. The composition as in claim 10, wherein A is $C_3$ alkylene.

12. The composition as in claim 10, wherein A is $C_4$ alkylene.

* * * * *